(12) United States Patent
Greenberg et al.

(10) Patent No.: US 6,669,964 B2
(45) Date of Patent: Dec. 30, 2003

(54) COMPOSITION FOR SOLUBILIZING SALICYLIC ACID

(75) Inventors: Stephen Greenberg, Paterson, NJ (US); Al-Nisa Ward, Paterson, NJ (US); Robert Sabo, Paterson, NJ (US)

(73) Assignee: Lipo Chemicals, Inc., Paterson, NJ (US)

( * ) Notice: Subject to any disclaimer, the term of this patent is extended or adjusted under 35 U.S.C. 154(b) by 24 days.

(21) Appl. No.: 09/875,382

(22) Filed: Jun. 6, 2001

(65) Prior Publication Data

US 2002/0187171 A1 Dec. 12, 2002

(51) Int. Cl.[7] .................. A61K 9/18; A61K 47/34; A61K 47/32; A61K 47/36
(52) U.S. Cl. .................. 424/499; 424/501; 424/69; 514/859
(58) Field of Search .................. 514/844, 845, 514/846, 847, 848, 859, 880–81, 937–38, 951; 424/443, 445, 499, 501, 61, 63–64, 69

(56) References Cited

U.S. PATENT DOCUMENTS 5,234,682 A * 8/1993 Macchio et al. ............ 424/489
5,449,519 A * 9/1995 Wolf et al. .................. 424/401

* cited by examiner

Primary Examiner—Edward J. Webman
(74) Attorney, Agent, or Firm—Ezra Sutton

(57) ABSTRACT

A composition for solubilizing and stabilizing salicylic acid for use in an anhydrous liquid precursor solution for use in the formulation of dermatological, cosmetic, toiletry and personal care products. The anhydrous liquid composition comprises butylene glycol acting as a solubilizer agent being in the range of 5.0% to 30.0% by weight of the composition; glycereth-26 acting as a solubilizer agent being in the range of 40.0% to 70.0% by weight of the composition; and salicylic acid for treating and preventing skin-related problems being in the range of 1.0% to 40.0% by weight of the composition.

9 Claims, 1 Drawing Sheet

SALICYLIC ACID SOLUBILITY CHART
FOR SOLUBILIZING SALICYLIC ACID THEREIN

| COMPOUNDS | Ex. A | Ex. B | Ex. C | Ex. D | Ex. E | Ex. F | Ex. G |
|---|---|---|---|---|---|---|---|
| Butylene Glycol | 10.0% | 20.0% | - | - | - | - | 10.0% |
| Propylene Glycol | - | - | 70.0% | - | - | - | - |
| Glycereth - 26 (Liponic EG-1) | 60.0% | 50.0% | - | - | - | - | - |
| Glycereth - 7 (Liponic EG-7) | - | - | - | - | - | - | 60.0% |
| Polyethylene Glycol 600 | - | - | - | 70.0% | - | - | - |
| Polyethylene Glycol 400 | - | - | - | - | 70.0% | - | - |
| Polyethylene Glycol 200 | - | - | - | - | - | 70.0% | - |
| Salicylic Acid | 30.0% | 30.0% | 30.0% | 30.0% | 30.0% | 30.0% | 30.0% |
| TOTALS | 100.0% | 100.0% | 100.0% | 100.0% | 100.0% | 100.0% | 100.0% |

SALICYLIC ACID SOLUBILITY CHART
FOR SOLUBILIZING SALICYLIC ACID THEREIN

| COMPOUNDS | Ex. A | Ex. B | Ex. C | Ex. D | Ex. E | Ex. F | Ex. G |
|---|---|---|---|---|---|---|---|
| Butylene Glycol | 10.0% | 20.0% | - | - | - | - | 10.0% |
| Propylene Glycol | - | - | 70.0% | - | - | - | - |
| Glycereth - 26 (Liponic EG-1) | 60.0% | 50.0% | - | - | - | - | - |
| Glycereth - 7 (Liponic EG-7) | - | - | - | - | - | - | 60.0% |
| Polyethylene Glycol 600 | - | - | - | 70.0% | - | - | - |
| Polyethylene Glycol 400 | - | - | - | - | 70.0% | - | - |
| Polyethylene Glycol 200 | - | - | - | - | - | 70.0% | - |
| Salicylic Acid | 30.0% | 30.0% | 30.0% | 30.0% | 30.0% | 30.0% | 30.0% |
| TOTALS | 100.0% | 100.0% | 100.0% | 100.0% | 100.0% | 100.0% | 100.0% |

FIG. 1

COMPOSITION FOR SOLUBILIZING SALICYLIC ACID

BACKGROUND OF THE INVENTION

1. Field of Invention

A composition for solubilizing and stabilizing salicylic acid for use in making dermatological, cosmetic, toiletry and personal care products for increased efficacy of the product. More particularly, the combination of anhydrous solvents, such as butylene glycol and glycereth-26, provides a stable solution of salicylic acid.

The use of salicylic acid for treating dandruff, acne, skin wrinkling, skin pigmentation, warts, freckles or skin-related problems are well known in the preparation of cosmetic and dermatologic formulations. Salicylic acid is usually in crystalline form and is not sufficiently soluble in water or oils traditionally used in the cosmetic and dermatological preparations. Typical problems which occur when using salicylic acid in making cosmetic and dermatologic products is that the salicylic acid tends to crystalize out of the various compositions, which significantly reduces the bioavailability of salicylic acid for treating or preventing the aforementioned skin problems. Further, salicylic acid provides formulations that form crystals on standing and precipitate out within the solution, which are unpleasant with regard to texture and appearance from the users point of view.

There remains a need for solubilizing salicylic acid for use in making cosmetic and dermatological products for increased product efficacy. The salicylic acid is solubilized and made stable within the cosmetic and dermatological formulations by the use of anhydrous solvents, such as butylene glycol and glycereth-26.

2. Description of the Prior Art

The use of salicylic acid in cosmetic and dermatologic formulas having various product formulations have been disclosed in the prior art. For example, U.S. Pat. No. 6,159,479 to PINZON discloses hydrous salicylic acid solutions for cosmetic and/or dermatological formulations. One of the formulations includes a coupler ingredient. This prior art patent does not disclose or teach the composition of the present invention having anhydrous solvents, such as butylene glycol and glycereth-26, for stabilizing salicylic acid for use in making various products.

U.S. Pat. No. 3,694,547 to FORSTHOFF, assigned to LEVER BROTHERS company of New York, N.Y., discloses an anti-dandruff hair preparation having salicylic acid therein. This prior art patent does not disclose or teach the composition of the present invention having anhydrous solvents, such as butylene glycol and glycereth-26, for stabilizing salicylic acid for use in making various products.

U.S. Pat. No. 4,835,148 to BARFORD et al discloses shampoo compositions having water-insoluble particulate anti-inflammatory agents therein. One of the shampoo embodiments includes anti-dandruff agents being salicylic acid and other chemical ingredients. This prior art patent does not disclose or teach the composition of the present invention having anhydrous solvents, such as butylene glycol and glycereth-26, for stabilizing salicylic acid for use in making various products.

U.S. Pat. No. 5,328,690 to SIKES discloses polyamino acid dispersants used in cosmetic products such as shampoos. One of the shampoo formulations includes an anti-dandruff agent being salicylic acid. This prior art patent does not disclose or teach the composition of the present invention having anhydrous solvents, such as butylene glycol and glycereth-26, for stabilizing salicylic acid for use in making various products.

U.S. Pat. Nos. 5,393,519; 5,587,154; and 5,665,267 to DOWELL et al, all assigned to HELENE CURTIS, INC., of Chicago, Ill., all disclose shampoo compositions having suspending agents therein. One of the anti-dandruff agents used in their anti-dandruff shampoos is salicylic acid. None of their examples of shampoo compositions include the composition of the present invention having anhydrous solvents, such as butylene glycol and glycereth-26, for stabilizing salicylic acid for use in making various products.

U.S. Pat. No. 5,973,000 to MAGARA et al discloses a hair revitalization tonic composition containing a lipid derivative therein. The composition includes salicylic acid and butylene glycol in its general formula. This prior art patent does not disclose or teach the composition of the present invention having anhydrous solvents, such as butylene glycol and glycereth-26, for stabilizing salicylic acid for use in making various products.

None of the aforementioned prior art patents teach or disclose the combination of ingredients for a composition having anhydrous solvents, such as butylene glycol and glycereth-26, for stabilizing a solution of salicylic acid within the formulation of the present invention.

Accordingly, it is an object of the present invention to provide cosmetic and dermatologic preparations having a stable and solubilized salicylic acid formulation therein for an increased efficacy of the product in treating and preventing skin-related problems, such as dandruff, acne, skin wrinkling, skin pigmentation, warts, freckles and the like.

Another object of the present invention is to provide salicylic acid having a stable and solubilized 30.0% (w/w) solution using anhydrous solvents, such as butylene glycol and glycereth-26 in the formulation of cosmetic and dermatologic preparations in order to prevent the settling-out or precipitation of the salicylic acid within the formula solution.

Another object of the present invention is to provide a stabilized solution of salicylic acid which does not form crystals on standing and can go through numerous freeze-thaw cycles without any precipitation of the salicylic acid from the cosmetic and dermatologic formulations.

Another object of the present invention is to provide a stabilized and solubilized salicylic acid solution having an increased bioavailability of salicylic acid compound or its derivatives for an increased efficacy in treating and preventing skin-related problems when using a nominal amount of the cosmetic and dermatologic formulation.

A further object of the present invention is to provide cosmetic and/or dermatologic preparations having salicylic acid therein that can be easily produced in an automated and economical manner and is readily affordable by the user.

SUMMARY OF THE INVENTION

In accordance with the present invention, there is provided a composition for solubilizing and stabilizing salicylic acid for use in an anhydrous liquid precursor solution for use in the formulation of dermatological, cosmetic, toiletry and personal care products. The anhydrous liquid composition comprises butylene glycol acting as a solubilizer agent being in the range of 5.0% to 30.0% by weight of the composition; glycereth-26 acting as a solubilizer reagent being in the range of 40.0% to 70.0% by weight of the composition; and salicylic acid for treating and preventing skin-related problems being in the range of 1.0% to 40.0% by weight of the composition.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein:

FIG. 1 is a chart showing various anhydrous solvents that solubilized salicylic acid into an anhydrous liquid precursor solution at specific % by weight of the precursor solution.

DETAILED DESCRIPTION OF THE PREFERRED EMBODIMENT

In accordance with the present invention, there is provided a composition for solubilizing and stabilizing salicylic acid for use in an anhydrous liquid system in the formulation of dermatologic, cosmetic, toiletry, and personal care products which include one or more anhydrous solvents for acting as solubilizer agents, such as butylene glycol and glycereth-26; and salicylic acid for treating and preventing skin-related disorders and problems. Alternatively, propylene glycol may be used in place of butylene glycol. Other anhydrous solvents may be used in place of glycereth-26 (sold by LIPO CHEMICAL Company under the trade name LIPONIC EG-1®), such as glycereth-7 (sold by LIPO CHEMICAL Company under the trade name LIPONIC EG-7®), polyethylene glycol 200, polyethylene glycol 400 and polyethylene glycol 600, as shown in FIG. 1. FIG. 1 represents a salicylic acid solubility chart showing the various anhydrous solvents that solubilize salicylic acid into an anhydrous liquid precursor solution at specific percentages by weight of the precursor solution.

The butylene glycol has a range of 5.0% to 30.0% by weight of the anhydrous liquid composition and a preferred range of 10.0% to 20.0% by weight of the anhydrous liquid composition. The glycereth-26 has a range of 40.0% to 70.0% by weight of the anhydrous liquid composition and a preferred range of 55.0% to 65.0% by weight of the anhydrous liquid composition. The salicylic acid has a range of 1.0% to 40.0% by weight of the anhydrous liquid composition and a preferred range of 25.0% to 30.0% by weight of the anhydrous liquid composition.

This anhydrous liquid precursor solution is added to a base composition of a dermatological, cosmetic, toiletry or personal care product formulation to form such products as lipsticks, foundation powders, rouge make-up, eye make-up, eye liner, eye shadow, shampoo, conditioners, hair colorings, soaps and the like. Typically, this anhydrous liquid composition is absorbed onto a polymer substrate, such as nylon 6/12 in order to make a usable powder additive containing 15.0% salicylic acid. Other polymer substrate materials can be used in place of nylon 6/12 such as acrylics, polyesters, cellulose or other plastic polymers when making the additive composition.

This additive composition includes butylene glycol or propylene glycol for acting as a solubilizer agent being in the range of 2.5% to 15.0% by weight of the additive composition and having a preferred range of 5.0% to 10.0% by weight of the additive composition; an anhydrous solvent selected from the group consisting of glycereth-26, glycereth-7, polyethylene glycol 200, polyethylene glycol 400, and polyethylene glycol 600 for acting as a solubilizer agent being in the range of 20.0% to 35.0% by weight of the additive compositions, and having a preferred range 27.5% to 32.5% by weight of the additive composition; and salicylic acid for treating and preventing skin-related problems being in the range of 0.5% to 20.% by weight of the additive composition, and having a preferred range of 12.5% to 15.0% by weight of the additive composition. The additive composition also includes a polymer substrate for receiving therein the butylene glycol or the propylene glycol, one or more of the anhydrous solvents and the salicylic acid therein all combined being in the range of 40.0% to 60.0% by weight of the additive composition and having a preferred range 47.5% to 52.5% by weight of the additive composition to form a composition for use in making a dermatologic, cosmetic, toiletry and personal care products.

Alternate Embodiment

The anhydrous liquid precursor solution can also be formulated with only one anhydrous solvent and the salicylic acid. The anhydrous solvent may be selected from the group consisting of propylene glycol, glycereth-26, glycereth-7, polyethylene glycol 200, polyethylene glycol 400 and polyethylene glycol 600 for acting as a solubilizer agent being in the range of 40.0% to 70.0% by weight of the anhydrous liquid composition and a preferred range of 55.0% to 65.0% by weight of the anhydrous liquid composition. The salicylic is in the range of 1.0% to 40.0% by weight of the anhydrous liquid composition and a preferred range of 25.0% to 30.0% by weight of the anhydrous liquid composition.

Additionally, an alternate additive composition can be formulated using only one anhydrous solvent selected from the group consisting of propylene glycol, glycereth-26, glycereth-7, polyethylene glycol 200, polyethylene glycol 400, and polyethylene glycol 600 for acting as a solubilizer agent being in the range of 20.0% to 35.0% by weight of the additive composition, and having a preferred range of 27.5% to 32.5% by weight of the additive composition; and salicylic acid for treating and preventing skin-related problems being in the range of 0.5% to 20.0% by weight of the additive composition, and having a preferred range of 12.5% to 15.0% by weight of the additive composition. The additive composition also includes a polymer substrate for receiving therein the butylene glycol or the propylene glycol, one or more the anhydrous solvents and the salicylic acid therein being in the range of 40.0% to 60.0% by weight of the additive composition and having a preferred range 47.5% to 52.5% by weight of the additive composition to form a composition for use in making a dermatologic, cosmetic, toiletry and personal care products.

Advantages of the Present Invention

Accordingly, an advantage of the present invention is that it provides for cosmetic and dermatologic preparations having a stable and solubilized salicylic acid formulation therein for an increased efficacy of the product in treating and preventing skin-related problems, such as dandruff, acne, skin wrinkling, skin pigmentation, warts, freckles and the like.

Another advantage of the present invention is that it provides for salicylic acid having a stable and solubilized 30.0% (w/w) solution using anhydrous solvents, such as butylene glycol and glycereth-26 in the formulation of cosmetic and dermatologic preparations in order to prevent the settling-out or precipitation of the salicylic acid within the formula solution.

Another advantage of the present invention is that it provides for a stabilized solution of salicylic acid which does not form crystals on standing and can go through numerous freeze-thaw cycles without any precipitation of the salicylic acid from the cosmetic and/or dermatologic formulations.

Another advantage of the present invention is that it provides for a stabilized and solubilized salicylic acid solution having an increased bioavailability of the salicylic acid compound or its derivatives for increased efficacy in treating and preventing skin-related problems when using a nominal amount of the cosmetic and dermatologic formulation.

A further advantage of the present invention is that it provides for cosmetic and/or dermatologic preparations having salicylic acid therein that can be easily produced in an automated and economical manner and is readily affordable by the user.

A latitude of modification, change, and substitutions intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An additive composition including an anhydrous liquid precursor solution having solubilized salicylic acid therein and a polymer substrate to be added to a base composition to make dermatologic, cosmetic, toiletry, and personal care products, comprising:
   a) butylene glycol or propylene glycol acting as a solubilizer agent being in the range of 2.5% to 15.0% by weight of the additive composition;
   b) an anhydrous solvent selected from the group consisting of glycereth-26, glycereth-7, polyethylene glycol 200, polyethylene glycol 400 and polyethylene glycol 600 for acting as a solubilizer agent being in the range of 20.0% to 35.0% by weight of the additive composition;
   c) salicylic acid for treating and preventing skin-related problems being in the range of 0.5% to 20.0% by weight of the additive composition;
   d) said salicylic acid being solubilized by said solubilizer agents for forming free salicylic acid molecules within said additive composition; and
   e) a polymer substrate for receiving therein said butylene glycol or said propylene glycol, one or more of said anhydrous solvents and said free salicylic acid molecules therein and being in the range of 40.0% to 60.0% by weight of said additive composition for use in making dermatological, cosmetic, toiletry, and personal care products.

2. An additive composition in accordance with claim 1, wherein said butylene glycol or said propylene glycol has a range of 4.5% to 5.5% by weight of the additive composition.

3. An additive composition in accordance with claim 1, wherein said one or more anhydrous solvents has a range of 27.5% to 42.5% by weight of the additive composition.

4. An additive composition in accordance with claim 1, wherein said salicylic acid has a range of 12.5% to 15.0% by weight of the additive composition.

5. An additive composition in accordance with claim 1, wherein said additive precursor is added to said base composition for use in making such products as lipsticks, foundation powders, rouge make-up, eye make-up, eye line and eye shadow.

6. An additive composition in accordance with claim 1, wherein said polymer substrate is selected from the group consisting of nylon, acrylic, polyester, cellulose and other polymeric materials.

7. An additive composition in accordance with claim 1, wherein said polymer substrate is nylon 6/12.

8. An additive composition in accordance with claim 1, wherein said polymer substrate has a preferred range of 48.0% to 52.0% by weight of the additive composition.

9. An additive composition in accordance with claim 6, wherein said additive precursor is added to said base composition for use in making such products as shampoos, conditioners, creams, lotions, and liquid soaps.

* * * * *